United States Patent [19]
Strauss et al.

[11] Patent Number: 5,831,067
[45] Date of Patent: Nov. 3, 1998

[54] AGENT FOR STIMULATING ANIMAL CELL DIVISION

[75] Inventors: Michael Strauss; Andre Lieber, both of Berlin, Germany

[73] Assignee: Max-Planck-Gesellschaft zur Förderung der Wissenschaften e.V., Germany

[21] Appl. No.: 511,836

[22] Filed: Aug. 7, 1995

Related U.S. Application Data

[63] Continuation-in-part of Ser. No. 107,983, Aug. 16, 1993, abandoned.

[30] Foreign Application Priority Data

Dec. 18, 1991 [DE] Germany .......................... 41 42 452.2

[51] Int. Cl.$^6$ .............................. C07H 21/00; C12P 19/34
[52] U.S. Cl. ........................................ 536/24.5; 435/91.31
[58] Field of Search .............................. 435/172.1, 172.3, 435/91.1, 91.31, 240.2; 536/24.5

[56] References Cited

U.S. PATENT DOCUMENTS 5,026,637  6/1991  Soule et al. ................................ 435/29

OTHER PUBLICATIONS

Finley et. al. (1989) Cell. 57, 1083–1093.
Khokhart et. al. (1989) Science 243, 947–950.
Lee et. al. (1987) Nature 329, 642–645.
Mayne et. al. (1986) Exper. Cell. Res. 162, 530–538.
Uhlmann et. al. (1990) Chem. Rev. 90(4), 543–584.
Weinberg (1990) TIBS 15, 199–202.
Woodworth et. al. (1988) Canc. Res. 48, 4620–4628.
Hara et al. Cooperative effect of antisense–Rb and antisense–p53 oligomers on the extension of life span in human diploid fibroblasts, TIG–1 Biochem. Biophys. Res. Commun. vol. 179 528–534, 1991.
Lee et al. The retinoblastoma susceptability gene encodes a nuclear phosphoprotein associated with DNA binding activity. Nature vol. 329 642–645, 1987.
Serrano et al. A new regulatory motif in cell–cycle control causing specific inhibition of cyclin D/CDK4 Nature vol. 366 704–707, 1993.
Meinkoth et al. Hybridization of nucleic acids immobilized on solid supports. Analytical Biochemistry vol. 138 267–284, 1984.
Wagner et al. Potent and selective inhibition of gene expresssion by an antisense hepanucleotide Nature Biotechnology vol. 14 840–844, 1996.
Chen et al. High efficiency trnasformation of mammalian cells by plasmid DNA. Molecular and Cellular Biology vol. 7 pp. 2745–2752, 1987.
Hatzfeld et al. Release of early human hematopoietic progenitors from quiescence by antisense transforming growth factor beta–1 or Rb oligonucleotides. J. Experimental Medicine vol. 174 pp. 925–929, 1991.
Dunnet al. Targeting bacteriophage T7 RNA polymerase to the mammalian cell nucleus. Gene vol. 6 pp. 259–266, 1988.

*Primary Examiner*—George C. Elliott
*Assistant Examiner*—John S. Brusca
*Attorney, Agent, or Firm*—Londa and Traub LLP

[57] ABSTRACT

Agents for stimulating the dividing activity of mammalian cells are presented, which have as an active substance a nucleotide sequence with a complimentary sequence (antisense) to a domain of the mRNA of tumor suppressor retinoblastoma or p16 genes acting on cell dividing activity. For Rb, the agents are nucleotide sequences 5'-GGTTTTGGGCGGCATGAC-3' (SEQ ID NO: 1) and 5'-CTCAGTAAAAGTGAACGA-3' (SEQ ID NO: 2); a nucleotide sequence comprising 49 base pairs, wherein the domain of the mRNA comprises nucleotides 124 to 152; and a 360 base pair nucleotide wherein the domain of the mRNA comprises an Hpa I restriction endonuclease site, an ASP718 endonuclease site, a portion of the 5' untranslated domain of the Rb gene, and a first exon of the Rb gene. For p16, the agent comprises GATCCATGCT GCTCC (SEQ ID NO: 3).

11 Claims, 3 Drawing Sheets

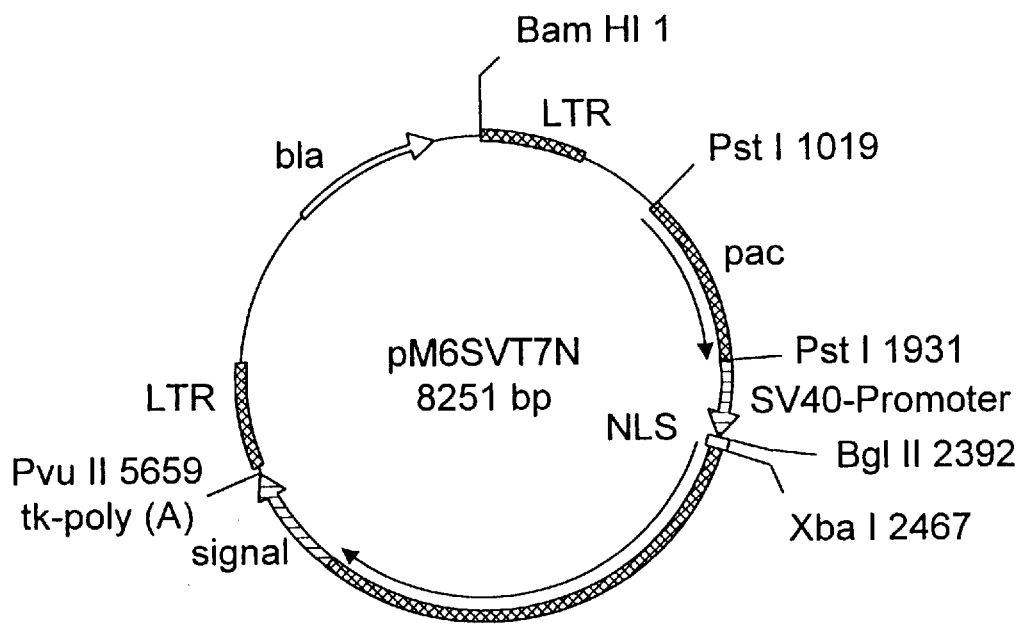
F I G. 1
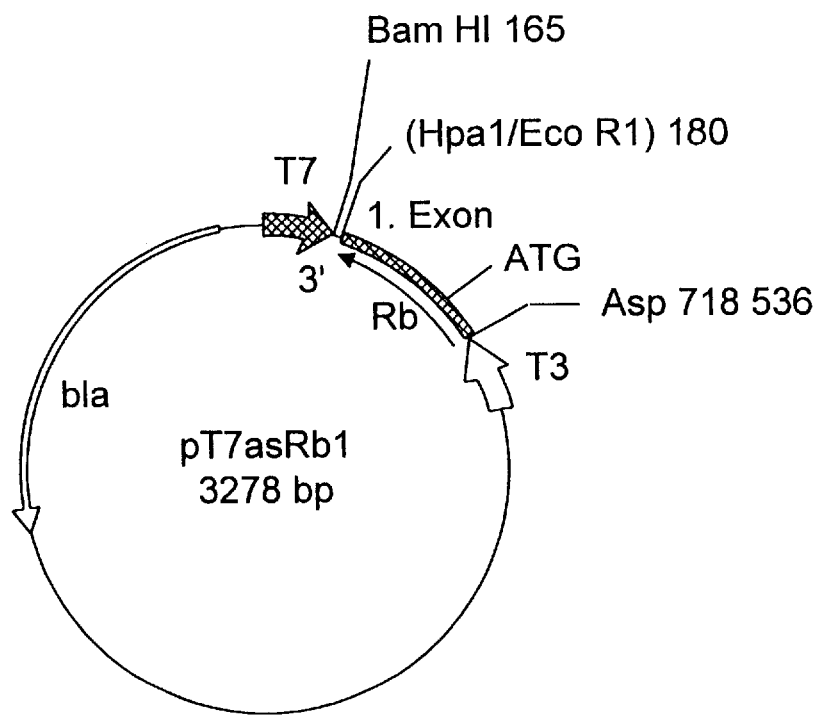
F I G. 2

5,831,067

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: mRNA ( i i i ) ANTI-SENSE: YES ( x i ) SEQUENCE DESCRIPTION: SEQ ID NO: 1:

GGTTTTGGGC GGCATGAC                                           18

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: mRNA ( i i i ) ANTI-SENSE: YES ( x i ) SEQUENCE DESCRIPTION: SEQ ID NO: 2:

CTCAGTAAAA GTGAACGA                                           18

( 2 ) INFORMATION FOR SEQ ID NO: 3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: mRNA ( i i i ) ANTI-SENSE: YES ( x i ) SEQUENCE DESCRIPTION: SEQ ID NO: 3:

GATCCATGCT GCTCC                                                  15

( 2 ) INFORMATION FOR SEQ ID NO: 4:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: mRNA ( i i i ) ANTI-SENSE: YES ( x i ) SEQUENCE DESCRIPTION: SEQ ID NO: 4:

GUUUUGGGCG GCAUCUGAUG AGUCCGUGAG GACGAAACGC CUUUCCGCG          49

( 2 ) INFORMATION FOR SEQ ID NO: 5:

( i ) SEQUENCE CHARACTERISTICS:
        ( A ) LENGTH: 15 base pairs (B) TYPE: nucleic acid
(C) STRANDEDNESS: single
(D) TOPOLOGY: linear (ii) MOLECULE TYPE: mRNA (iii) ANTI-SENSE: YES (xi) SEQUENCE DESCRIPTION: SEQ ID NO: 5:

GATCACATCT GATCC 15

AGENT FOR STIMULATING ANIMAL CELL DIVISION

This application is a continuation-in-part of application for U.S. patent Ser. No. 08/107,983, filed Aug. 16, 1993, now abandoned, which was the National Stage of PCT/EP92/02929, filed on Dec. 17, 1992.

SPECIFICATION

The invention relates to an agent for stimulating the dividing activity of animal and human cells, as well as to a method for using this agent. It can be used in fundamental biological and medical research, as well as in biotechnology and the pharmaceutical industry.

For clarifying fundamental biological processes as well as for using animal cells for biotechnological purposes, cells are required, which can be cultured for any length of time in artificial media. The unlimited cell-dividing ability is a criterion of tumor cells. However, cells in the "premalignant" state can also be immortal. In principle, the development of an immortal cell is based on genetic changes, which lead to a change in the function of one or several proteins, which are essential for the negative regulation of cell division.

Immortal cell lines can either be obtained directly from certain tumors or are formed in a roundabout way from primary cells, which were isolated from certain tissues. The spontaneous coming into being of an immortal cell line is an extremely rare event, since presumably at least two mutations are required for this. In the past, therefore, tumor viruses were frequently used as inductors of immortalization. However, these had the disadvantage that they frequently also caused unwanted tumorigenic changes in the cell. In the GDR Economic Patent 265 165, the use of the recombinants with the gene for the large T antigen of the polyoma virus has already been proposed for improving the immortalizing method. By these means, the problem of effectively immortalizing, without simultaneous tumorigenic change, was solved in principle. However, the rate of cell division is usually not affected by this method.

Many animal and human cells have a dividing potential limited to about 50 to 60 divisions without immortalization.

The longer viability frequently is desirable but not absolutely essential. However, the full utilization of the actual dividing potential is also difficult in many cell types, since it depends on an optimum supply of growth factors. Accordingly, in many cell types, the in vitro dividing activity is found to be limited to only a few cycles. An urgent problem for the biotechnological utilization of cell cultures consists of finding a basic solution for establishing cells of different organs with maximum utilization of their natural dividing potential and, as far as possible, additional stimulation of the cell division with respect to its rate.

The objects of the invention therefore are the development and application of an agent for generally stimulating the dividing activity of animal and human cells in the culture with respect to the full utilization of the natural dividing potential as well as to the speed of the cell cycle.

The inventive agent is characterized in that it contains as active substance one or several nucleotide sequences with a complementary sequence (anti-sense) to certain domains or all domains of the mRNA of tumor suppressor genes or other genes acting negatively on the cell division activity. The anti-sense nucleotide sequence consists preferably of a synthetic oligonucleotide having a length of at least 15 nucleotides, a length of 18 to 21 nucleotides being preferred.

The oligonucleotide must be present in nuclease-resistant form, the phosphothioate being particularly appropriate.

As anti-sense nucleotides sequences, especially sequences, which are complementary to a domain of the 5' end, the domain around the start codon, a domain of an exon or a domain at an intron-exon transition of the gene in question, are used. Preferably, complementary sequences to the tumor suppressor genes, retinoblastoma gene p16 gene, p53 gene or the E-cadherin are selected. Examples of concrete sequences of the effective substance in the inventive agent are 5'-GGTTTTGGGCGGCATGAC-3'(SEQ. ID NO: 1) and 5'-CTCAGTAAAAGTGAACGA-3'(SEQ. ID NO: 2). An additional example is the sequence 5'-GATCCATGCTGCTCC-3'(SEQ. ID NO: 3). For preparing the agent, the inventive, anti-sense nucleotide sequence is brought into solution, preferably into aqueous solution.

The following more detailed information is provided for using the agent to stimulate cell dividing activity:

Oligonucleotides are synthesized by known methods. In order to stimulate the cell-dividing activity of a cell culture, the cells, preferably growing while adhering to plastic, are treated with the selected anti-sense nucleotides. For this purpose, the oligonucleotides are sterilized by alcohol precipitation, dissolved in sterile, distilled water and added at a concentration of 5 to 30 $\mu$M to the culture medium without serum. The oligonucleotides can additionally be mixed with lipofectin, in order to achieve an even more effective absorption by the cells. The cells are incubated in the oligonucleotide-containing medium for several days. The cell count is determined daily in parallel batches in comparison with an untreated culture.

In primary human lung fibroblasts (HEL) a more rapid increase in the cell count in comparison with the control stands out after 3 days. After a single administration of oligonucleotides, this tendency continues for at least 7 days. With cells of this type, at least three times as many cells are attained with treated cells than with untreated cells within 10 days. Hybridizing clearly shows that the mRNA in the domain of the pairing with the anti-sense oligonucleotide is degraded.

Immunological protein detection shows that, no more than 3 days after the start of the treatment with oligonucleotides, the new synthesis of pRb has ceased completely.

If the treated culture is left for more than 7 days in the confluent state, dense islands of cells are formed, which are reminiscent of transformed foci, but actually contain no transformed cells. After about 14 days, the culture flasks are overgrown uniformly with a "multilayer" of cells. If the cells are stained and treated once again with oligonucleotide (5–30 $\mu$m), then the accelerated growth continues until the natural limit of about 60 cell divisions is reached. In a particular case, about 80 divisions can also be attained. However, since the treated cells divide more than twice as fast as the control cells, they end their life span appreciably earlier.

A comparison of different oligonucleotides with complementarity to different domains of the Rb-mRNA shows that approximately the same effect can be achieved with many of them. Generally however, an oligonucleotide with the following sequence, which is 5'-GGTTTTGGGCGGCATGAC-3'(SEQ. ID NO: 1) complementary to the domain around the start codon, proves to be particularly effective. This means that a maximum stimulating effect and a complete elimination of the pRb synthesis is attained at a relatively low concentration (10

μM) of the oligonucleotide. A combination of two oligonucleotides, for example, against the domain of the start codon and against an exon sequence, proves to be similarly effective at half the concentration (5 μM each). On the other hand, when oligonucleotides against other domains of the mRNA are used, higher concentrations (30 μM) are required.

Freshly prepared cells of other organs, such as the liver, which pass through only one or two cell division without treatment, can be cultured significantly longer after treatment with an Rb anti-sense oligonucleotide, the cell division being stimulated clearly. The inventive agent enables the number of cell divisions per unit time to be increased clearly. Its use also makes it possible to culture cells, which otherwise cannot be cultured. With this, great progress is made possible in biotechnological material production as well as in basic biological and medical research.

A further embodiment of the invention consists of producing the anti-sense nucleotide sequence in the very cell, which is to be cultured, instead of adding it for stimulating cell growth. This is achieved owing to the fact that a recombinant with expressible anti-sense sequence is introduced into the cells by transfection. In this case, the preferred sequence consists of 50 to 500 nucleotides.

The inventive recombinant contains the anti-sense nucleotide sequence in the reading direction after a strong promoter. The sequence preferably consists of complementary sequences of the tumor suppressor genes retinoblastoma gene, p16 gene p53 gene or E-cadherin. A particularly suitable sequence consists of the first 360 nucleotides of the mRNA-coding sequence of the retinoblastoma gene. As promoter for the recombinant, the T7 promoter, in conjunction with its homologous RNA polymerase, is particularly suitable.

BRIEF DESCRIPTION OF THE DRAWING

The invention is illustrated by reference to the drawing, wherein

FIG. 1 depicts a map of a vector expressing the T7 RNA polymerase gene;

FIG. 2 depicts a map of plasmid pT7asRb1;

Figure 3:
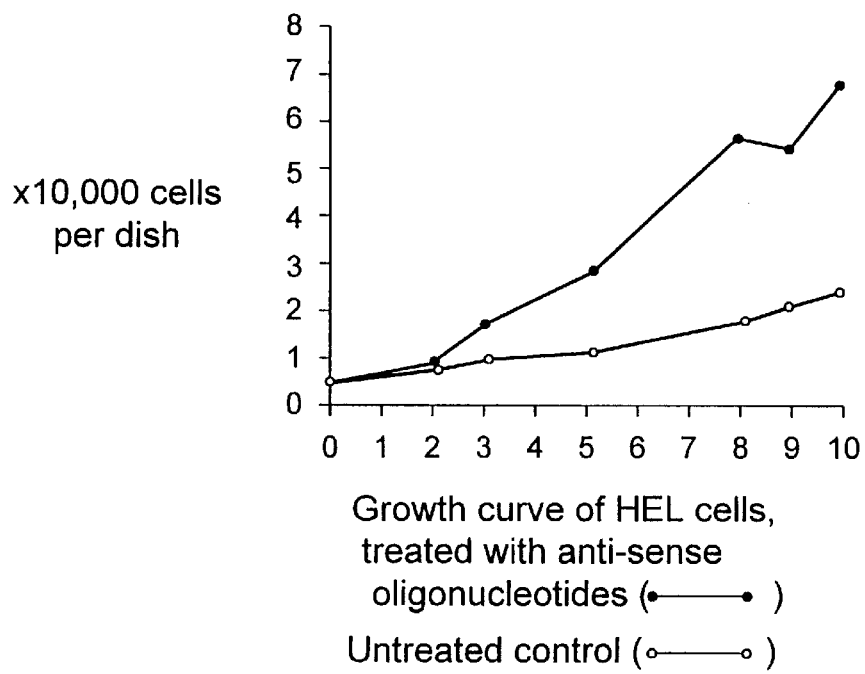
FIG. 3 is the growth curve of HEL cells treated with anti-sense oligonucleotides.

An example of the inventive recombinant is shown diagrammatically in FIG. 1. It consists of a 360 bp fragment of the human Rb gene with the 5' untranstranslated domain and the first exon, which is cloned in the anti-sense direction behind the T7 promoter in the pBluescript KS vector. The recombinant containing the antisense nucleotide sequence (RNA) or ribozyme against the p16 mRNA can be expressed by an adenovirus vector.

The following information is provided for using the agent:

A recombinant is prepared, a selected sequence, preferably 50 to 500 nucleotides long, being cloned from the tumor suppressor gene in question in anti-sense orientation behind a strong promoter. This recombinant is transfected preferably together with a selection marker and the gene of the T7 RNA polymerase by a known method into the cells in question. After selection for the presence of the marker (for example, pac), cells are obtained, the dividing activity of which is clearly stimulated.

The invention is to be described in greater detail in the following by embodiments.

EXAMPLE 1

An oligonucleotide with the sequence

5'GGTTTTGGGCGGCATGAC-3' (SEQ. ID NO:1)

is synthesized as phosphothioate by the well-known method using an automatic synthesis apparatus (Applied Biosystems) and dried. Approximately 100 O.D. units are dissolved in 100 μL of water, adjusted to 0.3M with sodium acetate and precipitated with 10 volumes of 96% ethanol at −70° C.

The precipitate is filtered off and dissolved in 0.5 mL of sterile water. After the concentration is measured, the solution is diluted to 1 μg/μL by the addition of water. Of this solution, 60 μL are diluted in 1 mL of cell culture medium. This corresponds to a concentration of 10 μM. This solution is added to the cells previously seeded in a 5 cm culture dish. In the Example, HEL cells are used at a density of 5×10$^4$ cells per dish. Eight dishes with oligonucleotide and 8 without (control) are prepared. After one hour, 1 mL of medium with 10% serum is added. On each succeeding day, the cells of one dish are harvested and counted in a cell-counting chamber. The results are shown graphically (see FIG. 2) and show a distinctly more rapid increase in the cell count from the second to the tenth day. After 10 days, a subculture is prepared, which is treated once again with oligonucleotide in the manner described above. The renewed, daily cell counting results in a curve of basically the same course, it being possible to recognize the difference after the first and second days more clearly than in the case of the first round.

EXAMPLE 2

An oligonucleotide with the sequence

5'-CTCAGTAAAAGTGAACGA-3' (SEQ. ID NO:2)

is produced as described under 1, prepared for use and added to the cell culture. The recording of a growth curve by daily cell counts reveals basically the same course of the curve as in FIG. 2, only 2.5 times, and not 3.5 times as many cells being present after 10 days.

EXAMPLE 3

The oligonucleotides of Examples 1 and 2 are used in combination at a concentration of 5 μM each and the cell count is determined daily. A steeper rise in the curve results, the cell count being 5 times that of the control cells after 10 days.

EXAMPLE 4

Preparation of the Recombinant Plasmids

The gene, which is by a nuclear localization signal-modified T7-RNA polymerase with the poly(A) signal of the thymidine kinase gene, was removed as BglII/PvuII fragment (3267 bp) from pMTT7N (Lieber et al. (1989) Nucl. Acids Res. 17: 8485–8493) and inserted in the retroviral vector pM6pac. In the resultant recombinant pM6SVT7N (FIG. 1), the gene of the T7-RNA polymerase is under the control of the "early" SV40 promotor. Cell clones, which express this recombinant, can be selected with puromycin. If necessary, the plasmid can be packed in a retrovirus. Of several, tested restriction fragments of the cDNA of the human retinoblastoma (Rb) gene, a 360 bp fragment (HpaI/Asp718), which covers the 5' untranslated domain and the first exon of the Rb gene, proves to be suitable for cell division stimulation by means of anti-sense Rb-RNA expression. This fragment was cloned in the pBluescript KS vector, which was split with Asp718/EcoRI and treated with phosphatase, and moreover by ligation of the cohesive Asp718 ends and subsequently filling the 5' projecting HpaI and EcoRI ends with Klenow polymerase and ring closure. By sequencing with T7 primer, a recombinant was selected, which contains the fragment of the Rb gene in the anti-sense (3'—5') direction behind the T7 promoter (pT7asRb1, FIG. 1). Modified T7-RNA polymerase, coexpressed in mammarian cells, highly effectively transcribes (more than 25,000 RNA molecules/cell) a gene under a T7 promoter (Lieber et al. (1993) Methods Enzymol. vol. 217, in press). Both plasmids were cleaned using a CsCl gradient.

Transfection By Means of Calcium Coprecipitation

Sixteen hours before the transfection, NIH 3T3 cells (embryonal mouse fibroblasts) are seeded at a cell density of $2.5 \times 10^5$ cells per 6 cm dish (25 cm$^2$). The cell culture medium (5 mL) is changed 3 hours before the transfection.

Water (225 µL) with 8 µg of pT7asRb1 and 2 µg of pM6SVT7N is added to a 15 mL falcon tube and 25 µL of 2.5M CaCl$_2$ are added. Under vortex mixing, 250 µL of 2×HBS buffer with a pH of 6.96 is added dropwise to the DNA-Ca solution (2×HBS: 280 mM NaCl, 50 mM HEPES, 1.5 mM Na$_2$HPO$_4$). The resulting precipitate is added immediately to the cells in the culture medium and left there for 12 to 16 hours. After that, the medium is changed.

After 48 hours, 3,000 cells are seeded per 6 cm dish. On the seventh day after transfection, very compact cell foci, which express the anti-sense Rb-RNA (T7 polymerase dependent), can be seen on a sparse lawn of untransfected 3T3 cells. The time required for these cells to double in number is reduced by a third, so that they rapidly overgrow the cells not expressed. The stress resistance (such as serum hunger) of these cells is also striking.

In a different protocol with selection, 50,000 cells per 6 cm dish were seeded 48 hours after transfection and 3 µg/mL puromycin were added to the cell culture medium. The selection medium was changed every 3 days. The bulk of the colonies formed had the morphology shown with formation of foci. One of these foci was isolated and expanded. No Rb protein could be detected in the Western blot of the cell lysate. It is interesting that anti-sense RNA, generated by a human Rb gene in mouse cells, has an expression-inhibiting action. There is 80% homology between human and mouse Rb cDNA.

The anti-sense Rb RNA-expressing 3T3 cells have characteristics of transformed cells; when cultured in soft agar, they form colonies with a frequency of $10^{-2}$ (untransfected control cells: $10^{-5}$).

Even more advantageous is the use of a construction, which brings about the synthesis of a gene-specific ribozyme in the cell. This construction, in which the actual ribozyme (RNA-splitting hammerhead RNA) is flanked by gene-specific sequences, is introduced into the cells by an optimized electroporation method, so that about 80% of all cells of effectively express the ribozyme thereby are stimulated to the maximum possible cell-dividing rate.

EXAMPLE 5

Figure 4:
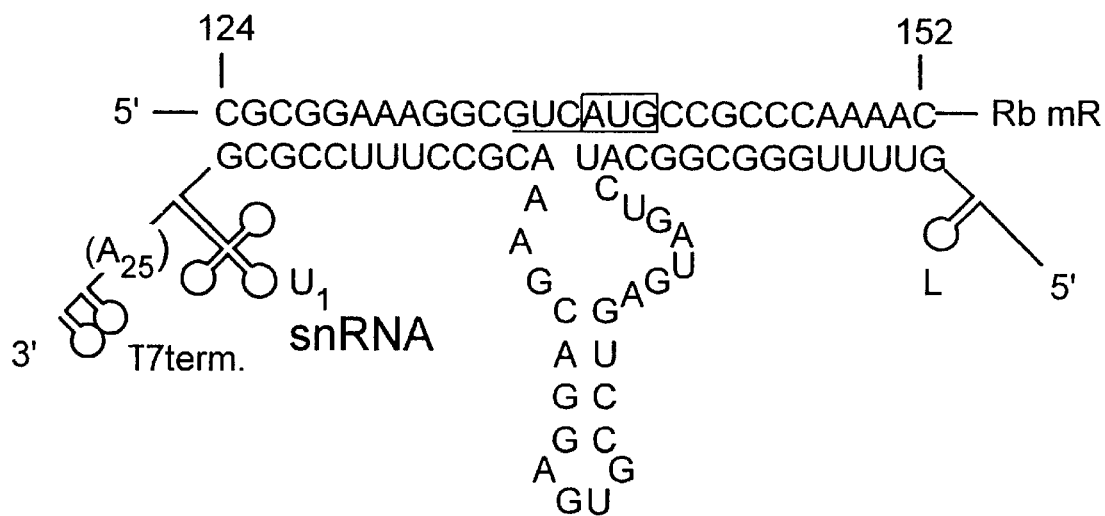
FIG. 4 is an anti-sense sequence to the nucleotides 124 to 152 of the mRNA with inclusion of sequence encoding a ribozyme (SEQ. ID NO:4)
Figure 5:
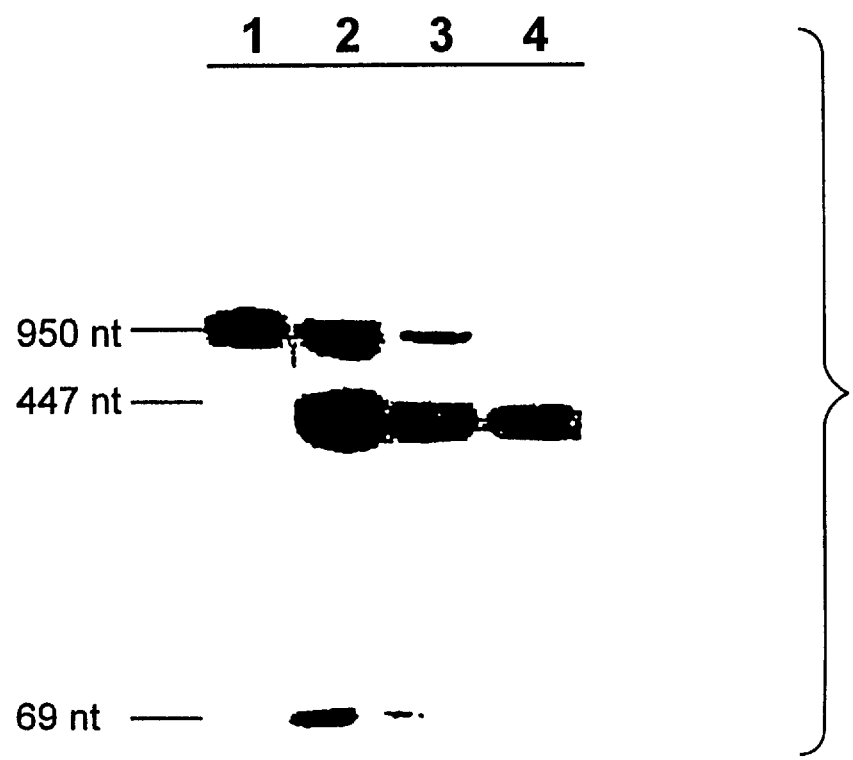
FIG. 5 shows the result of incubation of RNA regarding anti-sense with radioactively labeled Rb mRNA fragment of 950 nucleotides.

As target sequence, a domain of the Rb-mRNA was selected, where the nucleotide sequence GUC is present in the immediate vicinity of the AUG start codon as point of attack for a hammerhead ribozyme. An anti-sense sequence to the nucleotides 124 to 152 of the mRNA was produced synthetically with inclusion of a sequence, which encodes a ribozyme (FIG. 4) (SEQ. ID NO:4). This sequence, comprising 49 nucleotides in all, was produced in double-stranded form and cloned in the expression cassette of a vector, which permits expression of this sequence by a T7 promoter. This short and otherwise unstable sequence was embedded in other sequences which, after expression as RNA, form so-called "stem loops". An U1snRNA sequence brings about the localization of the RNA in the cell nucleus. A T7 terminator sequence makes possible the correct stop of the transcription. After cloning and reproduction of the recombinant plasmid (pT7RzRb1), at first the transcription was carried out in an in vitro batch with T7 polymerase RNA. This RNA was incubated with respect to the specificity of the anti-sense action with radioactively labeled Rb mRNA. The result is shown in FIG. 5. Track 1 shows the labeled Rb-RNA fragment of 950 nucleotides. Tracks 2 to 4 show the result of the incubation of the Rb-RNA with the ribozyme after 30 minutes at 37° C. The ribozyme:Rb-RNA ratio was 1:5 (Track 2), 1:2.5 (Track 3) and 1:1 (Track 4), the amount of ribozyme being kept constant and the Rb-RNA concentration being varied. The test demonstrates the functioning capability of the construction.

The recombinant pT7RzRb was introduced together with a plasmid, which codes for T7 polymerase (pMTT7N), by electroporation into CHO cells. The following conditions were determined to be optimum: 2 µg of DNA with $1 \times 10^5$ cells in 50 µL of DME medium without serum in a 0.4 cm cuvette, 320 V, 25 µF. Immediately after the pulse (gene pulser, BioRad), the cells were taken up in preheated DMEM with 10% serum and plated out. The cell-dividing rate was determined in the form of a growth curve that is, by a daily cell count. After 3 days, there were twice as many cells in the culture flask than in the untreated control and, after 5 days, three times as many cells. In addition, the treated cells proved to be significantly more robust and insensitive to changes in pH and temperature.

EXAMPLE 6

An oligonucleotide with the sequence 5'-GATCCATGCTGCTCC- 3' (SEQ. ID NO:3) is synthesized as described in Example 1 and is used as follows:

The foregoing data show a 3–4 fold increase of stimulation of cell division.

It is worth to point out that a significant multiplication can thus be obtained at all in primary cells.

Primary human skin fibroblasts ($1 \times 10^5$) are sown in 5 cm culture dishes in a culture medium with serum. Nine dishes are used per experiment (3 treatments of 3 dishes each). After 24 hours the cells are washed free of the serum. 2 ml serum-free medium is added to each dish, together with 20 µg lipofectin and 10 µg oligonucleotide (15 mer). Three dishes are treated with antisense p16 oligonucleotide (5'-GATCCATGCTGCTCC-3' (SEQ. ID NO:3)), three dishes with a mutant oligonucleotide, (5'-GATCACATCTGATCC-3' (SEQ. ID NO:5)), and three control dishes without any oligonucleotide, and all are incubated. Finally the medium is changed and serum is added. Five days later the cells are trypsinated and are counted. The following results are obtained:

| | | | |
|---|---|---|---|
| Control (w/o oligonucleotide) | $1.3 \times 10^5$; | $1.8 \times 10^5$; | $1.6 \times 10^5$ |
| Mutant oligonucleotide | $1.5 \times 10^5$; | $2.1 \times 10^5$; | $1.8 \times 10^5$ |
| Antisense p16 oligonucleotide | $4.8 \times 10^5$; | $5.5 \times 10^5$; | $6.2 \times 10^5$ |

We claim:

1. An agent for stimulating the dividing activity of mammalian cells, comprising as an active substance a nucleotide sequence with a complementary sequence (anti-sense) to a domain of the mRNA of tumor suppressor retinoblastoma gene acting on cell dividing activity, wherein the nucleotide sequence consists of SEQ. ID NO.:1.

2. The agent of claim 1, wherein the cells are human cells.

3. An agent for stimulating the dividing activity of mammalian cells, comprising as an active substance a nucleotide sequence with a complementary sequence (anti-sense) to a domain of the mRNA of tumor suppressor retinoblastoma gene acting on cell dividing activity, wherein the nucleotide sequence consists of SEQ. ID NO.:2.

4. The agent of claim 3, wherein the cells are human cells.

5. An agent for stimulating the dividing activity of mammalian cells, comprising as an active substance a nucleotide sequence with a complementary sequence (anti-sense) to a domain of the mRNA of tumor suppressor p16 gene acting on cell dividing activity, wherein the nucleotide sequence consists of SEQ. ID NO.:3.

6. The agent of claim 5, wherein the cells are human cells.

7. An agent for stimulating the dividing activity of mammalian cells, comprising as an active substance a nucleotide sequence comprising 49 nucleotides with a complementary sequence (anti-sense) to a domain of the mRNA of tumor suppressor retinoblastoma gene acting on cell dividing activity, wherein the domain of the mRNA comprises nucleotides 124 to 152.

8. The agent of claim 7, wherein the cells are CHO cells.

9. A hammerhead ribozyme flanked by an agent for stimulating the dividing activity of mammalian cells, comprising as an active substance a nucleotide sequence comprising 49 nucleotides with a complementary sequence (anti-sense) to a domain of the mRNA of tumor suppressor retinoblastoma gene acting on cell dividing activity, wherein the domain of the mRNA comprises nucleotides 124 to 152, the ribozyme having a target located on the Rb gene where a GUC is adjacent to an AUG start codon.

10. An agent for stimulating the dividing activity of mammalian cells, comprising as an active substance a 360 base pair nucleotide sequence with a complementary sequence (anti-sense) to a domain of the mRNA of tumor suppressor retinoblastoma gene acting on cell dividing activity, wherein the domain of the mRNA comprises an Hpa I restriction endonuclease site, an ASP718 endonuclease site, a portion of the 5' untranslated domain of the Rb gene, and a first exon of the Rb gene.

11. The agent of claim 10, wherein the cells are mouse cells.

* * * * *

UNITED STATES PATENT AND TRADEMARK OFFICE
CERTIFICATE OF CORRECTION

PATENT NO.      : 5,831,067
DATED           : November 3, 1998
INVENTOR(S)     : Michael Strauss, Andre Lieber It is certified that an error appears in the above-identified patent and that said Letters Patent is hereby corrected as shown below:

On the title page item [63] should read as follows:

[63] Continuation-in-part of Ser.No. 107,983, Aug. 16, 1993, abandoned, which was a Continuation-in-part of PCT/EP92/02929, Dec. 17, 1992

Signed and Sealed this

Thirteenth Day of April, 1999

*Attest:*

Q. TODD DICKINSON

*Attesting Officer*         *Acting Commissioner of Patents and Trademarks*